United States Patent [19]

Lomard

[11] 4,232,019
[45] Nov. 4, 1980

[54] METHOD FOR THE TREATMENT OF MALE STERILITY

[75] Inventor: Jean-Pierre Lomard, Massy, France

[73] Assignee: Societe Anonyme dite: CM Industries, Paris, France

[21] Appl. No.: 52,109

[22] Filed: Jun. 26, 1979

[51] Int. Cl.² ............................................. A61U 27/00
[52] U.S. Cl. ................................................ 424/248.56
[58] Field of Search .................................... 424/248.56

[56] References Cited
PUBLICATIONS

Fromantin et al., Extrait de a Problems Actuel D'Endocrinologie et de Nutrition, pp. 44–55.

*Primary Examiner*—Stanley J. Friedman
*Attorney, Agent, or Firm*—Bacon & Thomas

[57] ABSTRACT

A method for the treatment of male sterility whereby 100 to 300 mg of a drug containing 3-morpholinoethylamino 4-methyl 6-phenylpyridazine are administered daily to the the patient by oral route.

1 Claim, No Drawings

METHOD FOR THE TREATMENT OF MALE STERILITY

The present invention relates to a method for treating male sterility.

Sterility may be defined as the incapacity to conceive during the normal sexual life; in a man, it is a deficiency in the sperm production, in quality and in quantity, which is the prime reason for male sterility.

According to T. R. HARRISON—"Principles of Internal Medicine"—the main causes for this sperm deficiency in the male subject are:

Hormone troubles (hypophyseal gonadotrophins)
Obstacles (such as tumors or traumatisms) in the sperm release passages.
Infections of the gonads, of the sperm passages and of their adnexa.
Certain therapeutics lowering the spermatogenesis (for example; a treatment against epilepsis).

It has been found that the product known as 3-morpholino-ethylamino 4-methyl 6-phenylpyridazine (hereinafter designated as 30038, and described in U.S. Pat. No. 4,169,158, issued Sept. 25, 1979, from application Ser. No. 820,489, filed July 29, 1977, when used by oral route in doses varying between 100 and 300 mg of active substance daily, could advantageously be used for treating male sterility.

The following tests illustrate the invention; these tests were carried out on male patients seeking advice on sterility in the couple for no apparent reason in their partner.

Said tests consisted in examining the sperm of the patients before and after the treatment; two samples of sperm were examined under the microscope before treatment and two samples after a six-week treatment of four 50 mg tablets daily. The criteria for a normal sperm as retained from this examination, are as follows:

Number of spermatoids per unit of volume (N): 60 millions/ml.
Mobility of the spermatoids (M): at least 60% of the spermatoids are still mobile 2 to 3 hours after the sperm has been collected.
Morphology of the spermatoids (Mo): at least 60% of the spermatoids examined should have a normal morphology.

The 13 examined (respectively numbered 3-6-7-8-9-10-11-12-13-14-15-17-18) answer to the folowinf etiological criteria (Table I)

TABLE I

|  | Oligospermia | % Mobility too low | % Normal morphology too low |
|---|---|---|---|
| No detectable cause | 3-6-7-8-18 | 6-7-8-18- | — |
| Varicocele operated 3 years or more before | 9-11-12- | 10-11- | 10 |
| After Medically treated prostatitis | 13-14- | 13-14-15- | — |
| Epileptic under specific treatment | 17- | 17- | — |

The results obtained for these different cases are given hereunder.

TABLE II (1) Number of spermatoids

| Observation No. | Number of Spermatoids Millions (M) per ml | | Improvement (M. Spermatoids/ml) |
|---|---|---|---|
| | Before treatment | After treatment | |
| 3 | 57 M. | 58 M. | +1 |
| 6 | 36 M. | 68 M. | +32 |
| 7 | 48 M. | 56 M. | +8 |
| 8 | 56 M. | 57 M. | +1 |
| 18 | 42 M. | 46 M. | +4 |
| 9 | 46 M. | 78 M. | +32 |
| 11 | 47 M. | 48 M. | +1 |
| 12 | 60 M. | 63 M. | +3 |
| 13 | 48 M. | 52 M. | +4 |
| 14 | 60 M. | 62 M. | +2 |
| 17 | 7 M. | 38 M. | 31 |

TABLE III (2) % SPERMATOIDS WITH NORMAL MOBILITY 2-3 hours after collection of the sperm).

| Observation No. | % Spermatoids offering a normal mobility | | Improvement |
|---|---|---|---|
| | Before treatment | After treatment | |
| 6 | 52% | 65% | +13% |
| 7 | 50% | 67% | +17% |
| 8 | 58% | 61% | + 3% |
| 18 | 50% | 56% | + 6% |
| 10 | 56% | 67% | +11% |
| 11 | 59% | 69% | +10% |
| 13 | 51% | 70% | +19% |
| 14 | 46% | 60% | +14% |
| 15 | 44% | 59% | +15% |
| 17 | 52% | 59% | + 7% |

TABLE IV (3) % Spermatoids with normal morphology

| Observation No. | Before treatment | After treatment | Improvement |
|---|---|---|---|
| 10 | 58 % | 81 % | +23 % |

The foregoing results call for the following remarks:

An improvement of the sperm "deficiencies" is noted in all the cases observed having received the treatment.

In general, the improvement observed is all the more important that the corresponding deficiency is more obvious.

Even in those case where one criterion or another may be considered as "normal", the said criterion (N, M and Mo) is improved by the treatment; for example, if the proportions of spermatoids with normal morphology were considered to be normal before the treatment, their examination after treatment shows an average improvement of 9.1%.

What is claimed is:

1. A method for the treatment of male sterility caused by dyspermatogeny, comprising orally administering daily to the sterile male from 100 to 300 mg of 3-morpholinoethylamino-4-methyl-6-phenylpyridazine or a pharmaceutically acceptable salt thereof.

* * * * *